US006272380B1

(12) United States Patent
Warman et al.

(10) Patent No.: US 6,272,380 B1
(45) Date of Patent: Aug. 7, 2001

(54) APPARATUS FOR TREATING ATRIAL TACHY ARRHYTHMIAS WITH SYNCHRONIZED SHOCKS

(75) Inventors: Eduardo N. Warman, Maple Grove; Michael R. S. Hill, Minneapolis, both of MN (US); David K. L. Peterson, Saugus, CA (US); Rahul Mehra, Stillwater; Luc R. Mongeon, Minneapolis, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/377,514

(22) Filed: Aug. 19, 1999

(51) Int. Cl.[7] .................................................. A61N 1/39
(52) U.S. Cl. .................................................. 607/5; 607/4
(58) Field of Search ............................................. 607/4, 5

(56) References Cited

U.S. PATENT DOCUMENTS

| Re. 36,765 | * | 7/2000 | Mehra ........................... 607/4 |
|---|---|---|---|
| 4,232,679 | | 11/1980 | Schulman . |
| 4,375,817 | | 3/1983 | Engle et al. . |
| 4,384,585 | | 5/1983 | Zipes . |
| 4,572,191 | | 2/1986 | Mirowski et al. . |
| 4,577,633 | | 3/1986 | Berkovits et al. . |
| 4,587,970 | | 5/1986 | Holley et al. . |
| 4,726,380 | | 2/1988 | Vollmann et al. . |
| 4,727,877 | | 3/1988 | Kallok . |
| 4,800,883 | | 1/1989 | Winstrom . |
| 4,830,006 | | 5/1989 | Haluska et al. . |
| 4,880,005 | | 11/1989 | Pless et al. . |
| 4,949,719 | | 8/1990 | Pless et al. . |
| 4,953,551 | | 9/1990 | Mehra et al. . |
| 5,007,422 | | 4/1991 | Pless et al. ........................ 128/419 D |
| 5,052,388 | | 10/1991 | Sivula et al. . |
| 5,074,301 | | 12/1991 | Gill . |
| 5,088,488 | | 2/1992 | Markowitz et al. . |
| 5,107,850 | | 4/1992 | Olive . |
| 5,161,527 | | 11/1992 | Nappholz et al. . |
| 5,163,427 | | 11/1992 | Keimel . |
| 5,188,105 | | 2/1993 | Keimel . |
| 5,411,524 | | 5/1995 | Rahul . |
| 5,464,431 | | 11/1995 | Adams et al. . |
| 5,545,186 | | 8/1996 | Olson et al. . |
| 5,620,471 | | 4/1997 | Duncan . |
| 5,674,249 | | 10/1997 | deCoriolis et al. . |
| 5,755,737 | | 5/1998 | Prieve et al. . |
| 5,846,263 | * | 12/1998 | Peterson et al. ........................ 607/14 |
| B1 4,830,006 | | 10/1997 | Haluska et al. . |
| B1 4,880,005 | | 10/1996 | Pless et al. . |

FOREIGN PATENT DOCUMENTS

| 9528987 | 2/1995 | (WO) . |
|---|---|---|
| 9528988 | 2/1995 | (WO) . |

OTHER PUBLICATIONS

"Synchronous Intracardiac Cardioversion" Zipes et al, Barold S. Serge, ed. Modern Cardiac Pacing. Mount Kisco, NY: Futura pub. Co. 1985, pp. 727–743.
U.S. Patent Application, SN 08/649,145, entitled "Prioritized Rule Based Method and Apparatus for Diagnosis and Treatment of Arrhythmias" filed May 14, 1996, Gillberg et al.

* cited by examiner

Primary Examiner—Carl Layno
(74) Attorney, Agent, or Firm—Girma Wolde-Michael

(57) ABSTRACT

An implantable anti-tachyarrhythmia device which delivers atrial cardioversion or defibrillation pulses heart in response to detection of atrial tachyarrhythmias. The pulses are synchronized to atrial and ventricular events in such a fashion as to assure they occur outside of the vulnerable periods associated with both chambers.

14 Claims, 11 Drawing Sheets

APPARATUS FOR TREATING ATRIAL TACHY ARRHYTHMIAS WITH SYNCHRONIZED SHOCKS

BACKGROUND OF THE INVENTION

This invention relates to devices which treat tachyarrhythmias (rapid heart rhythms), and more specifically, to methods to provide delivery of atrial cardioversion and defibrillation shocks at appropriate times relative to atrial and ventricular depolarizations.

It has long been recognized that synchronizing atrial and ventricular cardioversion to depolarizations in the chamber being treated improves efficacy of treatment. For example, synchronization of ventricular cardioversion shocks to sensed R-waves is disclosed in U.S. Pat. No. 4,375,817 issued to Engle et al. Synchronization of cardioversion shocks intended to treat atrial or ventricular tachycardia or fibrillation to detected R-waves is disclosed in U.S. Pat. No. 4,384,585, issued to Zipes. Synchronization of atrial cardioversion shocks to detected P-waves is disclosed in U.S. Pat. No. 4,572,191, issued to Mirowski et al.

Delivery of cardioversion or defibrillation shocks intended to terminate a tachyarrhythmia of one chamber unfortunately may induce a tachyarrhythmia in the other chamber. The risk associated with tachyarrhythmia induction in the ventricle is sufficiently great that it has long been recognized that atrial defibrillation pulses need to be timed to avoid the vulnerable period of the ventricle. The most common approach to accomplish this result has been to deliver the atrial defibrillation or cardioversion pulse closely synchronized to a sensed ventricular depolarization to avoid the ventricular vulnerable period, as disclosed in U.S. Pat. No. 4,384,585, issued to Zipes. Due to the fact that in the presence of high ventricular rates, the vulnerable period associated with one R-wave may extend to include the next R-wave, it has also long been recognized that the vulnerable period following a ventricular depolarization may extend to include the time of occurrence of the next subsequent ventricular depolarization in the presence of a sufficiently rapid ventricular rhythm. In such cases, there is no safe time for delivery of cardioversion pulse, as discussed in the article "Synchronous Intracardiac Cardioversion", by Zipes et al., published in *Modern Cardiac Pacing*, edited by Barold, Futura Publishing Co. 1985, pages 727–743.

Because cardioversion pulses synchronized to a ventricular rhythm which is too rapid may induce ventricular arrhythmias or fibrillation, implantable cardioverters have typically included some method to assure that a minimum R-R interval has elapsed as a prerequisite to delivery of a cardioversion shock. One such synchronization method which prevents delivery of a cardioversion pulse synchronized to a ventricular rhythm which is too rapid is to require that the shock be synchronized to a ventricular depolarization falling outside a defined refractory period defined following the immediately preceding ventricular depolarization, as in the Model 7210 implantable transvenous cardioverter manufactured by Medtronic, Inc. While the device could sense ventricular depolarizations during this refractory period and would initiate a new refractory period following such depolarizations, it would not deliver cardioversion pulses synchronized to such depolarizations,. As reflected in the above-cited article by Zipes et al, the transvenous cardioversion therapy provided by the model 7210 device could be employed to treat either ventricular or supraventricular tachyarrhythmias.

An alternative method for controlling the timing of an atrial defibrillation or cardioversion shock is to deliver the shock after a defined interval following a preceding R-wave, in the absence of a sensed ventricular depolarization, the defined interval being sufficiently long to prevent delivery during the vulnerable period associated with the preceding R-wave. Such a synchronization method is disclosed in U.S. Pat. No. 5,411,524, issued to Mehra. As disclosed in the Mehra patent, the defined interval may vary as a function of the sensed ventricular rate.

In the context of tachyarrhythmia treatment devices capable of sensing in both chambers, the opportunity is presented to require that delivered cardioversion shocks avoid the vulnerable periods of both the atria and ventricles. One device which accomplishes this result is disclosed in U.S. Pat. No. 5,007,422, issued to Pless et al. In the device disclosed in the Pless et al. patent, ventricular cardioversion shocks avoid the vulnerable periods of both chambers by means of the requirement that they are delivered synchronized to a slow ventricular tachycardia R-wave occurring outside the vulnerable period of the atrium. An alternative method to assure that delivered ventricular cardioversion shocks occur outside the vulnerable periods of both the atria and the ventricles is to deliver an atrial pacing pulse and synchronize to an R-wave occurring within 100 ms of the preceding atrial pacing pulse, as disclosed in U.S. Pat. No. 5,074,301, issued to Gilli et al. The same synchronization methods may correspondingly be employed to prevent delivery of an atrial cardioversion pulse during the vulnerable periods of either chamber.

SUMMARY OF THE INVENTION

The present invention provides an implantable atrial defibrillator with enhanced dual chamber synchronization of atrial defibrillation pulses. The device defines a first synchronization interval following an atrial event during which an atrial defibrillation pulse may be delivered and second and third synchronization intervals following a ventricular event during which an atrial defibrillation pulse may be delivered. An atrial defibrillation pulse may be delivered synchronized to a ventricular event occurring within the first synchronization interval or to an atrial event if the initiation of the first synchronization interval thereafter occurs within either the second or third synchronization intervals following the immediately preceding ventricular event.

The first synchronization interval is initiated on expiration of a time interval X1 following the sensed atrial event and expires on expiration of a time interval X2 following the sensed atrial event. X1 may expire synchronous to sensing a P wave, or following a delay thereafter. X2 preferably expires at less than the cycle length of the detected atrial tachycardia or fibrillation. The duration of the first synchronization interval between the expiration of intervals X1 and X2 may, for example, be 20 to 30 milliseconds. For example, in one implementation of the invention, X1 may expire on atrial sensing or shortly thereafter and X2 may expire prior to 50 milliseconds following atrial sensing. Alternatively, X2 may expire at a time following the detected P wave equal to the detected cycle length of the ongoing atrial tachyarrhythmia minus a delta of 20–50 milliseconds, and X1 may expire 20 to 30 milliseconds therebefore.

The second synchronization interval initiated on a ventricular event typically extends until expiration of a time interval X3 following the ventricular event which may be equal to, for example, 80 milliseconds or less in order to assure that the delivered atrial defibrillation or cardioversion pulse occurs closely coupled to the sensed ventricular event. Delivery of an atrial cardioversion or defibrillation pulse during the second synchronization interval is also preconditioned on expiration of a minimum interval X5 following the ventricular event preceding the ventricular event which initiated the second synchronization interval presently underway. This minimum interval may correspond to the duration of the ventricular refractory period. X5 may be, for example, 350 to 550 milliseconds.

The third synchronization interval begins on expiration of a time interval X4 following the immediately preceding ventricular event. X4 is preferably greater in duration than X5 and may be, for example, 400 to 600 milliseconds. X4 may correspond to the duration of the post-ventricular atrial refractory period.

In an alternative embodiment of the invention, rather than delivering the atrial defibrillation or cardioversion pulse on expiration of time interval X1, assuming that X1 is appropriately timed using the above limitations, the device may instead deliver the cardioversion or defibrillation pulse at the earliest point during the first synchronization interval which meets the above defined requirements. For example, the atrial cardioversion or defibrillation pulse may be delivered at the first point during the first synchronization interval which occurs prior to expiration of X3, timed from the immediately preceding ventricular event, and after expiration of X5 following the ventricular event preceding the ventricular event which initiated interval X3.

In a preferred embodiment of the invention, the dual chamber synchronization method of the present invention is incorporated into the device which employs multiple synchronization methods in turn, in an attempt to provide for safe and reliable atrial cardioversion and defibrillation. In such a device, the available synchronization methods may sequentially be employed for a sequence of a predetermined number of synchronization cycles each, with the device switching to successive synchronization methods following failure of the device to synchronize during the preset number of cycles allotted to the preceding synchronization method. The dual chamber synchronization method of the present invention may be employed as the first synchronization method attempted by the device or as a second or subsequent synchronization method attempted by the device. Typically, the synchronization methods will be ordered so that more restrictive synchronization methods are attempted first, with successively less restrictive synchronization methods attempted thereafter.

DETAILED DESCRIPTION OF THE PREFERRED EMBODIMENTS

Figure 1:
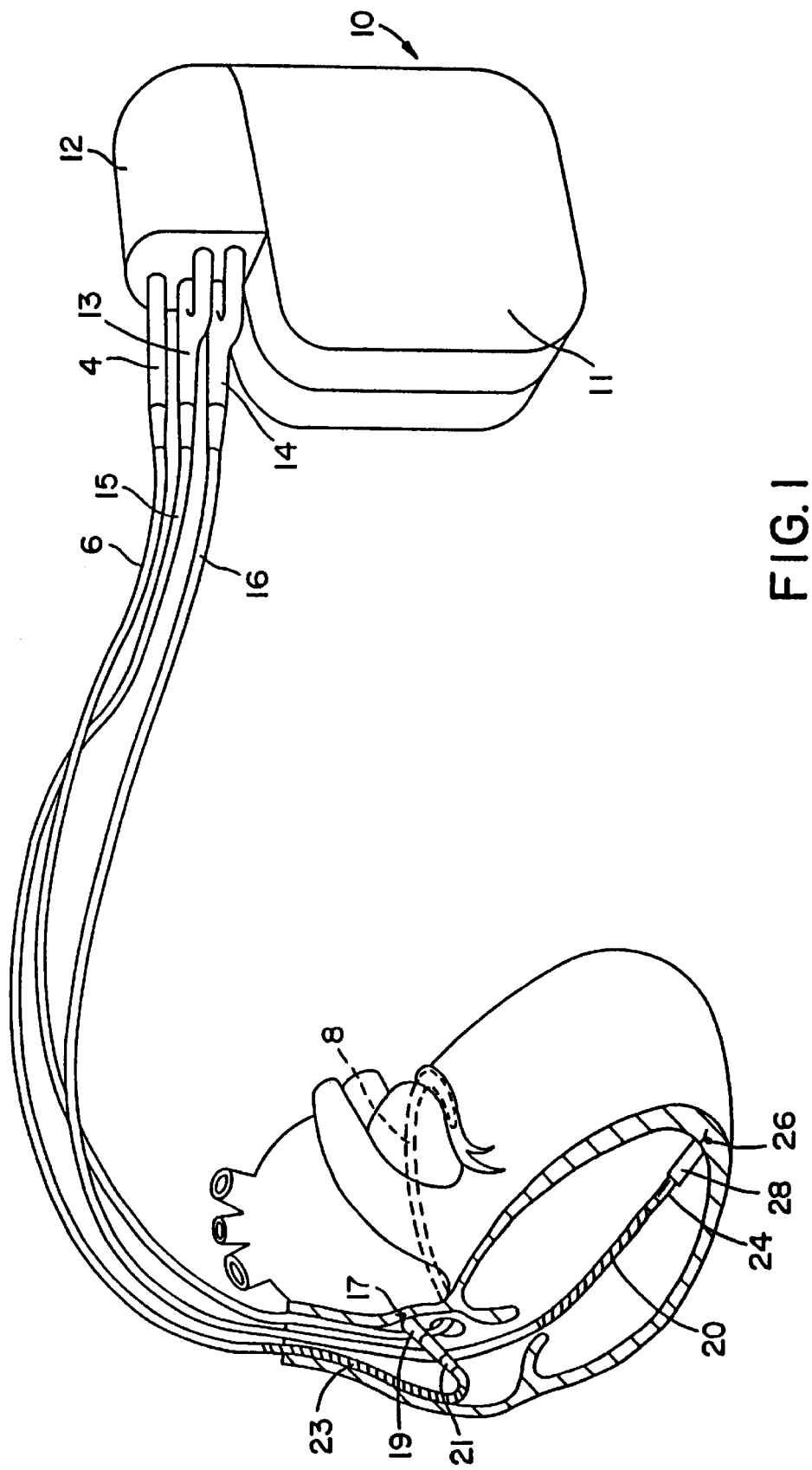
FIG. 1 illustrates a first embodiment of an implantable pacemaker/cardioverter/ defibrillator of a type appropriate for use in practicing the present invention, in conjunction with a human heart.

FIG. 1 illustrates a defibrillator and lead set according to the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coil electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector 13 which carries three electrical connectors, each coupled to one of the coiled conductors.

The coronary sinus lead includes an elongated insulative lead body 6, carrying one coiled conductor coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may op course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
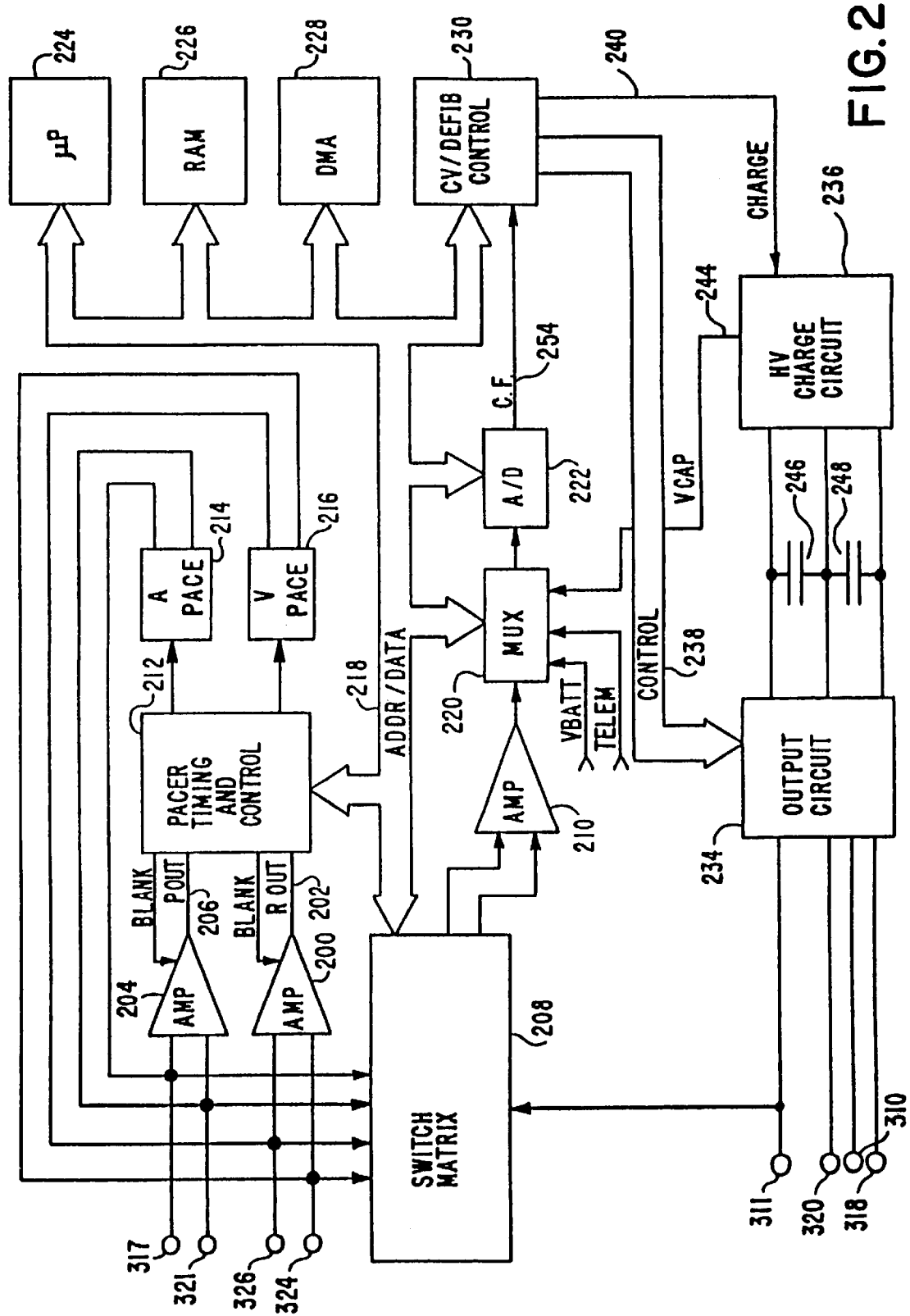
FIG. 2 illustrates a functional schematic diagram of an implantable pacemaker/cardioverter/defibrillator in which the invention may be practiced.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide antitachycardia pacing therapies, antitachycardia pacers which do not provide cardioversion or defibrillation, and devices which deliver different forms of antiarrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter /defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204. which preferably also takes the form of an automatic gain controlled amplifier providing an I! adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/ control circuitry 212 corresponding to the occurrences of sensed P-waves and R-waves and corresponding to the generation of cardiac pacing pulses. These interrupts are provided via data/address bus 218. Any necessary mathematical calculations to be per-formed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The present invention may employ any tachycardia detection algorithm known to the art to detect the occurrence of tachyarrhythmias. For example, the detection methods disclosed in U.S. Pat. No. 5,545,186 issued to Olson et al for detection of atrial fibrillation and tachycardias may be employed, or the method of U.S. Pat. application Ser. No. 08/649,145 fled May 14, 1996 by Gillberg et al, may be substituted for this detection method. The Olson patent and the Gillberg et al. application are hereby incorporated by reference in their entireties. Alternatively, other known detection algorithms for use in conjunction with implantable atrial cardioverters such as those disclosed in U.S. Pat. No. 5,464,431 issued to Adams et al, U.S. Pat. No. 6,161,527 issued to Nappholz et al, or U.S. Pat. No. 5,107,850 issued to Olive, all incorporated by reference in their entireties may also be employed. A device embodying the present invention may also include the ability to treat ventricular tachyarrhythmias, as discussed above. In the event such capability is desired, any of the prior art ventricular tachyarrhythmia detection methods may be employed, including those in the above cited Olson patent and Gillberg et al application, as well as the detection methods disclosed in U.S. Pat. No. 5,620,471 issued to Duncan, U.S. Pat. No. 5,830,006 issued to Haluska et al., U.S. Pat. No. 4,880,005 issued to Pless et al., and U.S. Pat. No. 5,560,369 issued to McClure et al., all incorporated by reference in their entireties as well. In addition, the device may be configured such that the patient initiates delivery of the therapy by means of an external controller, such that the device may not employ a detection method of its own as a prerequisite to a delivery of therapy. In this context, a patient activator as disclosed in U.S. patent application Ser. No. 08/764,865 by Prieve et al. filed on Dec. 16, 1996, incorporated by reference in its entirety herein may be employed. Alternatively, patient activators of the sort disclosed in U.S. Pat. No. 5,674,249 issued to DeCoriolis et al. or U.S. Pat. No. 4,262,679 issued to Schulman, all incorporated by reference in their entireties may instead be employed. The particular choice of patient activator is not critical to the success of the invention, and any workable method for initiating the delivery of the atrial cardioversion or defibrillation therapy may usefully be employed.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. Any known ventricular cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed. In addition, high frequency pulse bursts may be delivered to electrodes 317 and 321 to terminate atrial tachyarrhythmias, as described in PCT Patent Publication No. WO95/28987, filed by Duffin et al and PCT Patent Publication No. WO95/28988, filed by Mehra et al, both incorporated herein by reference in their entireties.

In the illustrated device, delivery of cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4.727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modem implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/ cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3A:
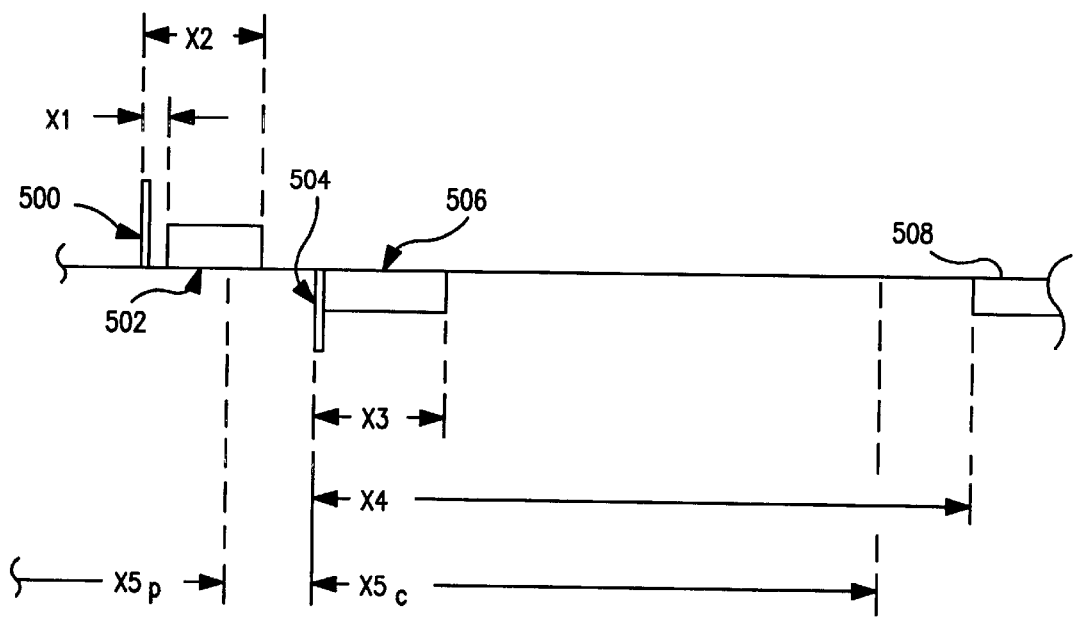
FIGS. 3A–3D illustrate a primary synchronization method that may be used by a device embodying the present invention.

FIGS. 3A through 3D illustrate the time periods and synchronization methods employed in a preferred embodiment of the present invention. In FIG. 3A, an atrial event 500 is illustrated which initiates the timing of a first synchronization interval 502, discussed above. First synchronization interval 502 is initiated on expiration of interval X1 after the atrial event 500 and expires on expiration of interval X2 after the atrial event 500. Following ventricular event 504, a second synchronization interval 506 is timed, extending from the ventricular event 504 until the expiration of a time interval X3 thereafter. In response to ventricular event 504, the device also defines interval X4, on the expiration of which the third synchronization interval 508 described above is initiated. Third synchronization interval 508 extends until expiration of the underlying ventricular pacing escape interval, unless terminated earlier by ventricular sensing or delivery of a cardioversion or defibrillation pulse. Also initiated in response to ventricular event 504 is an interval $X5_c$ which defines a minimum interval between R waves as described above. Also illustrated is the expiration point of the corresponding minimum interval $X5_p$ timed from the ventricular event preceding ventricular event 504. The synchronization methods employed in this preferred embodiment are intended to assure delivery of an atrial cardioversion pulse outside of the vulnerable periods of both the atria and the ventricles if possible, by preferentially delivering cardioversion pulses only during the overlap of the defined first and second synchronization intervals or during the overlap of the defined first and third synchronization intervals, subject to the requirement that a minimum interval has elapsed from any immediately preceding ventricular depolarization. The cardioversion pulse is delivered synchronized to the initiation of the one of the two overlapping synchronization intervals which begins later.

Figure 3B:
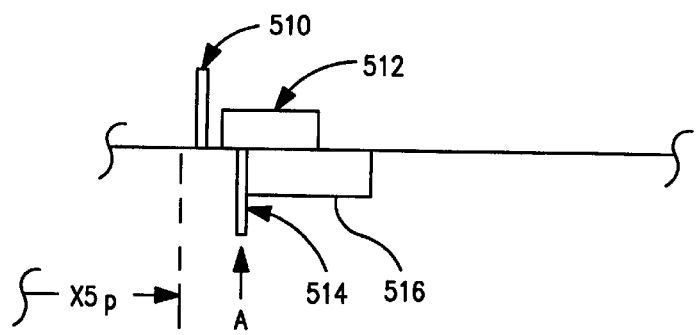

FIG. 3B illustrates the operation of the device in delivering an atrial cardioversion or defibrillation pulse synchronized to a sensed or paced ventricular event occurring during a first synchronization interval. An atrial event 510 triggers timing of a first synchronization interval 512. A ventricular sensed or paced event 514 occurs within first synchronization interval 512, after the expiration of the preceding minimum interval $X5_p$, initiated on the ventricular event preceding ventricular event 514. In this circumstance, the device may deliver an atrial cardioversion or defibrillation pulse at point A, synchronized to sensed or paced ventricular event 514. The timing of a second synchronization interval 516 is also illustrated, initiated concurrent with ventricular event 514.

Figure 3C:
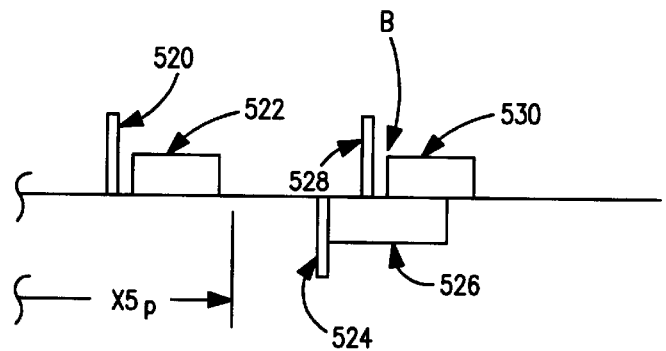

FIG. 3C illustrates synchronization of an atrial defibrillation or cardioversion pulse to an atrial event occurring during a second synchronization interval as described above. An atrial event 520 initiates timing of a first synchronization interval 522. Synchronization to a ventricular event during first synchronization interval 522 would not be possible, as minimum interval $X5_p$ timed from the ventricular event preceding event 524 has not expired. On occurrence of ventricular event 524, timing of a second synchronization interval 526 is initiated. An atrial event occurs at 528, triggering timing of first synchronization interval 530. On occurrence of the leading edge of first synchronization interval 530, which occurs during second synchronization interval 526 and after expiration of the minimum interval $X5_p$ timed from the ventricular event preceding event 524, an atrial cardioversion or defibrillation pulse may be delivered at point B.

Figure 3D:
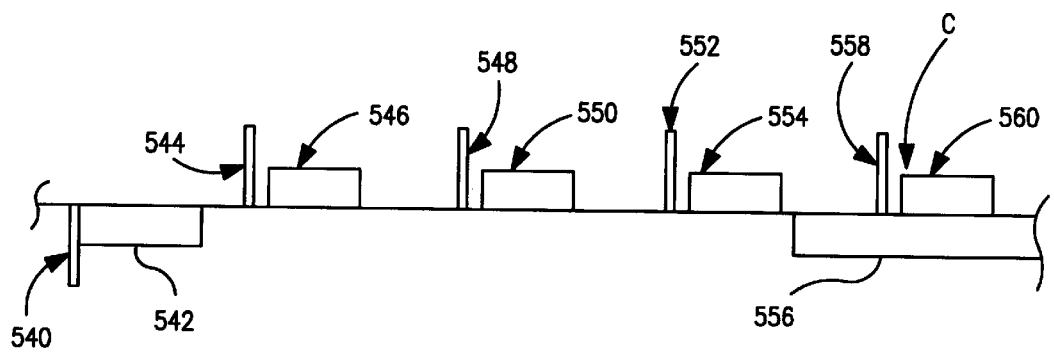

FIG. 3D illustrates synchronization of an atrial cardioversion or defibrillation pulse to an atrial depolarization sensed during a third synchronization interval, as described above. A ventricular event occurs at 540, initiating timing of a first synchronization interval 542. Atrial events occur at 544, 548, 552 and 558, followed by timing of corresponding first synchronization intervals at 546, 550, 554 and 560 as discussed above. Because the initiation of first synchronization intervals at 546, 550, 554 and 560 occurs outside of first synchronization interval 542, shocks are not delivered synchronized to their initiation times. Because the initiation of first synchronization interval 560 occurs during third synchronization interval 556, an atrial cardioversion or defibrillation pulse may be delivered at C, synchronous with the initiation of first synchronization interval 560.

Figure 4A:
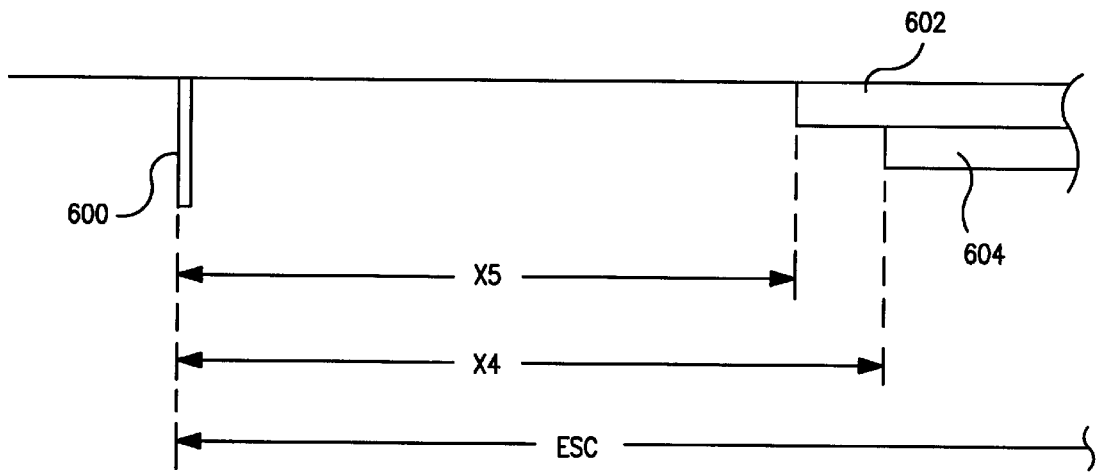
FIGS. 4A–4B illustrate time intervals employed in additional synchronization methods that may be used by a device embodying the present invention.
Figure 4B:
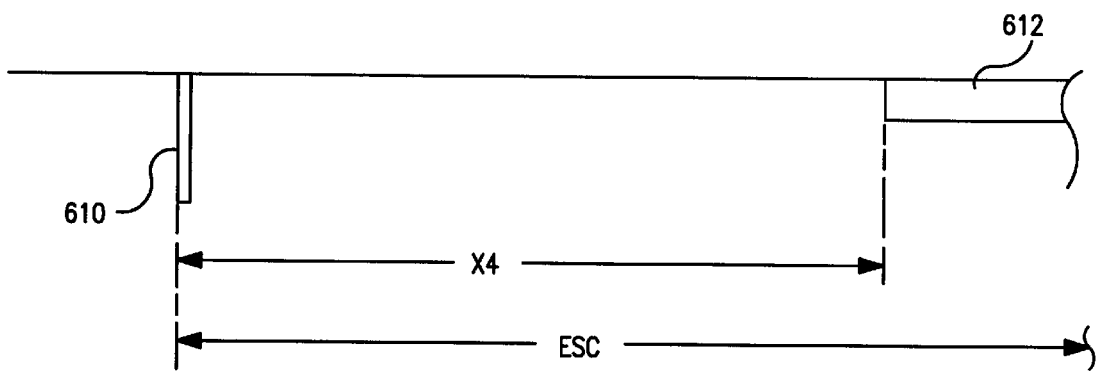

FIGS. 4A and 4B illustrate the time intervals associated with additional synchronization methods that may be used in conjunction with the synchronization method illustrated in FIGS. 3A through 3D. In FIG. 4A, a less restrictive synchronization method is illustrated. In conjunction with a device employing the present invention, this less restrictive synchronization method might be employed in the event that the synchronization method illustrated in FIGS. 3A through 3D failed to allow for synchronization within a predetermined number of synchronization cycles. At 600, a ventricular event occurs, initiating timing of minimum time interval X5 and time interval X4, which on expiration initiate a synchronization intervals 602 and 604, both of which extend until expiration of the ventricular escape interval (ESC) corresponding to the base VVI pacing rate, which is also initiated on occurrence of ventricular event 600. In this alternative synchronization method, an atrial cardioversion or defibrillation pulse may be delivered in response to any ventricular event sensed during synchronization interval 602 following expiration of minimum time interval X5 or may be synchronized to any atrial event occurring synchronization interval 604, initiated after expiration of time interval X4. This synchronization method allows for delivery of an atrial defibrillation or cardioversion pulse outside the vulnerable periods of both the atrium and the ventricle in some cases, but does not require that the defibrillation or cardioversion pulse be delivered outside the vulnerable period associated with the atrium in all cases.

FIG. 4B discloses a more restrictive synchronization method which might be used in conjunction with the synchronization method illustrated in FIGS. 3A through 3D.

This synchronization method allows delivery of atrial cardioversion or defibrillation pulses only outside both the vulnerable period of the atrium and the ventricle period of the ventricle. In response to a ventricular event at 610, time interval X4 is initiated, upon the expiration of which synchronization interval 612, is initiated, which in turn extends until expiration of the underlying ventricular escape interval (ESC), which is also initiated on occurrence of the ventricular event at 610. An atrial defibrillation or cardioversion pulse in this method may be delivered only synchronized to an atrial event occurring during synchronization interval 612. In the context of a device employing the present invention, this synchronization method might be employed as the initial attempt at synchronization, with synchronization according to the method illustrated in FIGS. 3A–3D and/or according to FIG. 4A attempted following a failure of the synchronization method illustrated in FIG. 4B to allow for a synchronization during a preset number of synchronization cycles.

Figure 5:
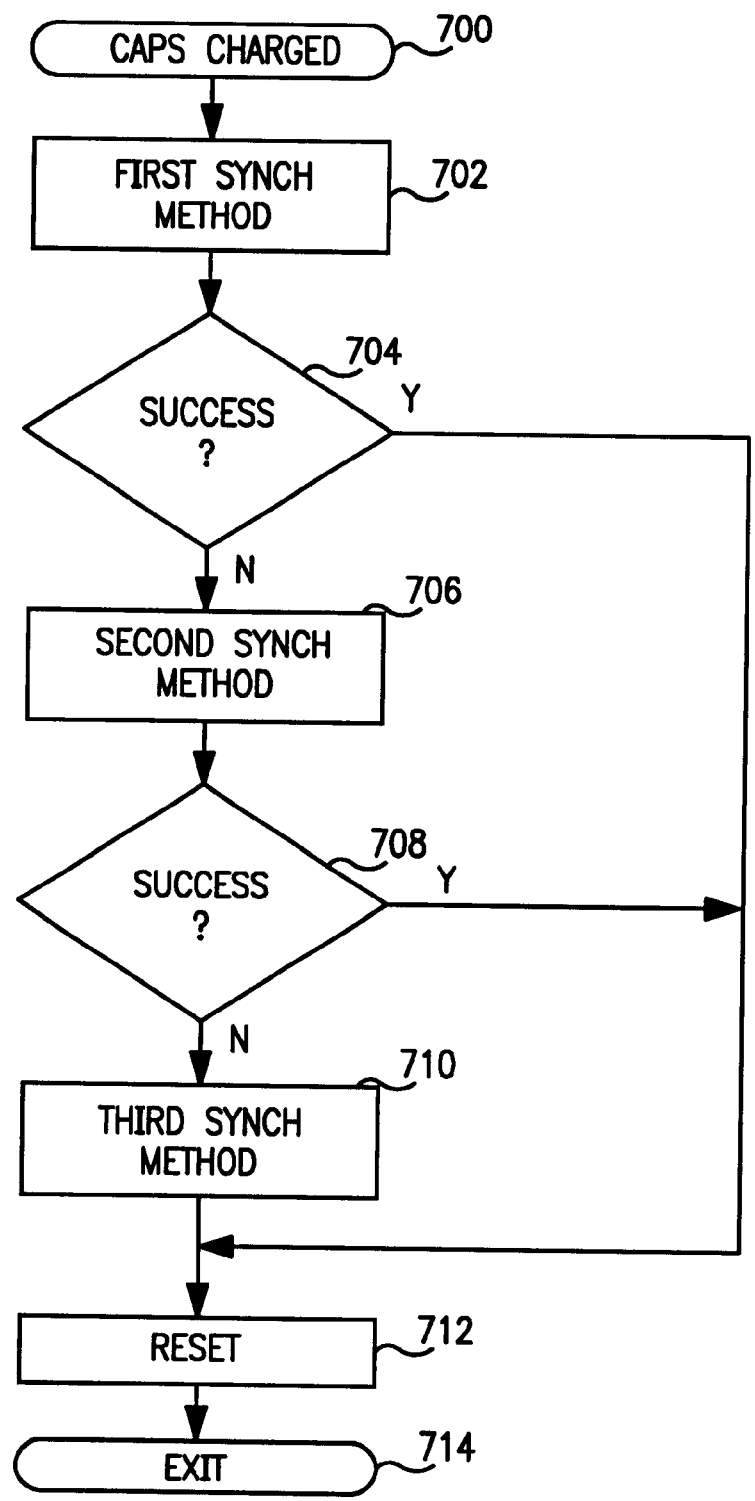
FIG. 5 is a functional flowchart illustrating over-all operation of the synchronization methods of a preferred embodiment of a device according to the present invention.

FIG. 5 illustrates the overall operation of a device employing the present invention, in which multiple synchronization methods are sequentially attempted in order to provide atrial cardioversion or defibrillation. In response to the output capacitors being charged to their programmed voltage at 700, the first synchronization method is attempted at 702. This synchronization method may, for example, be the synchronization method illustrated in FIGS. 3A–3D or alternatively may be a more restrictive synchronization method, for example, the method illustrated in FIG. 4B. If the device determines that synchronization was successful at 704, in response to an atrial cardioversion or defibrillation pulse being delivered, the detection criteria are reset at 712 and the device returns to normal operation, attempting to determine whether or not the atrial tachyarrhythmia has successfully been terminated. In the event that the first synchronization method was unsuccessful, the second synchronization method is attempted at 706. If the initial synchronization method is the method illustrated in FIGS. 3A–3D, for example, the second synchronization method might be the method illustrated in FIG. 4A. Alternatively, if a more restrictive initial synchronization method is employed at 704, the synchronization method of FIGS. 3A–3D might be employed at 706. If the device determines that the synchronization method was successful at 708, the device resets the detection criteria and returns to normal function attempting to determine whether the atrial tachyarrhythmia was successfully terminated. If synchronization according to the second synchronization method was unsuccessful, a third synchronization method might be employed at 710, and so forth. In conjunction with the present invention, any number of synchronization methods might successfully be employed, with the understanding that following application of the final synchronization method, the device will terminate its attempts to treat the detected atrial tachyarrhythmia, regardless of success of the final synchronization method. In such a device, subsequent attempts to terminate the tachyarrhythmia may be preconditioned to expiration of a defined time interval, as disclosed in U.S. patent application Ser. No. 08/764,865 by Prieve et al. filed on Mar. 18, 1997, incorporated herein by reference in its entirety or may be preconditioned on detection of a new arrhythmia, following spontaneous termination of the previously detected atrial tachyarrhythmia.

Figure 6A:
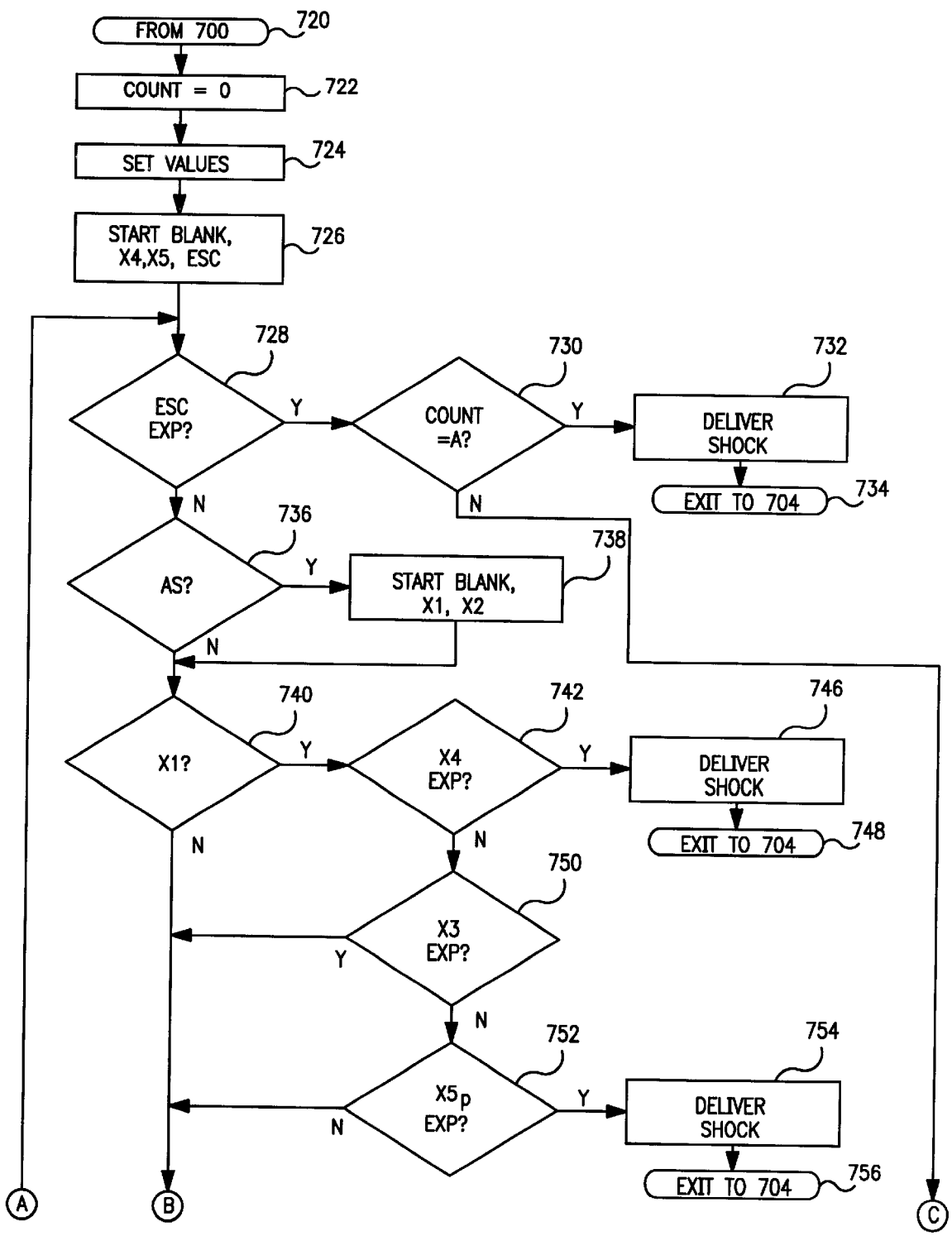
FIGS. 6A, 6B and 6C are a functional flowchart illustrating operation of the primary synchronization method of FIGS. 3A–3B.
Figure 6B:
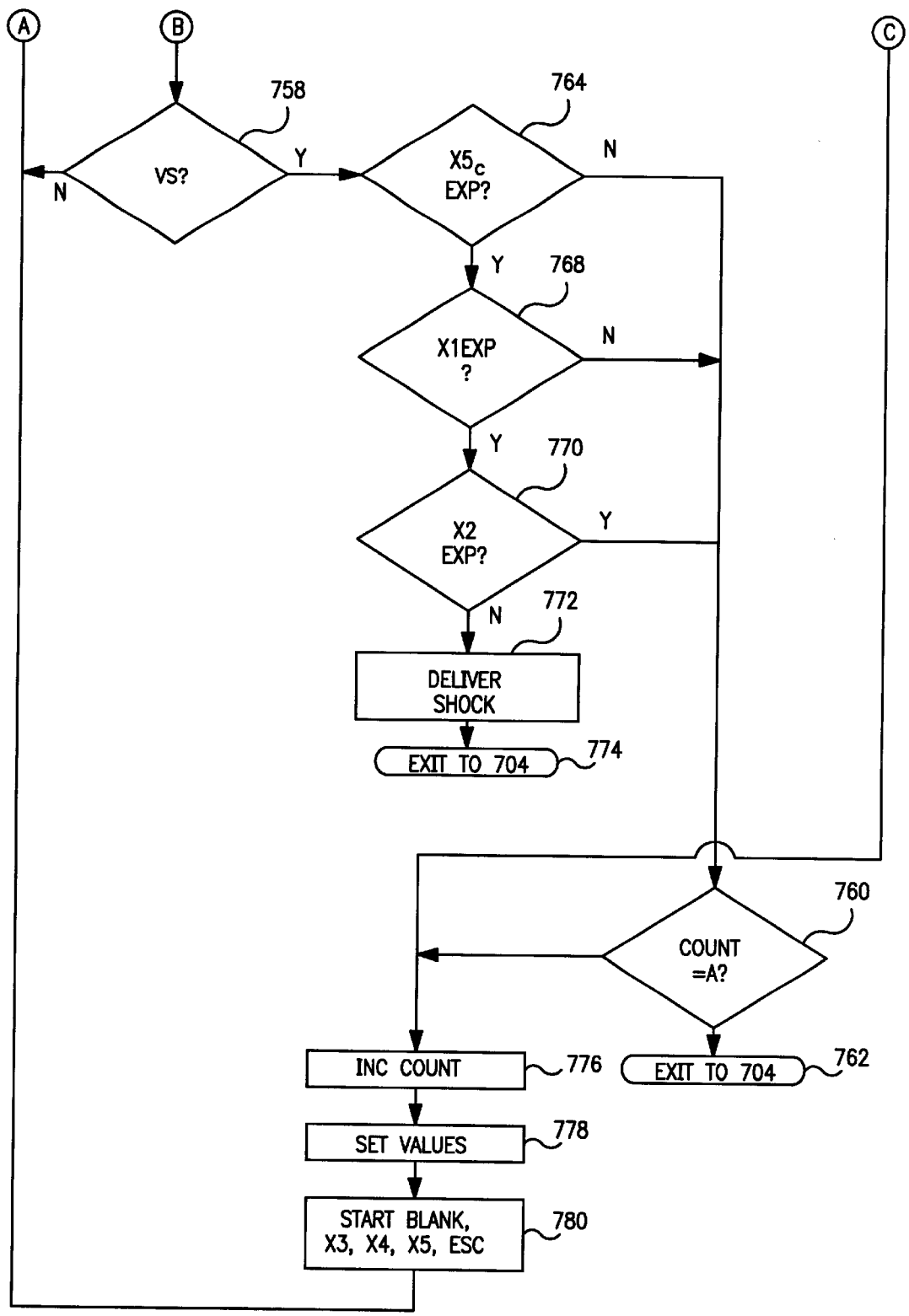

FIGS. 6A and 6B together are a functional flow chart which illustrates the operation of the synchronization method of the preferred embodiment of the present invention, corresponding to that illustrated in FIGS. 3A–3D. In conjunction with FIGS. 6A and 6B, it should be assumed that the synchronization method according to FIGS. 3A–3D is employed as the initial synchronization method, initiated in response to charging of the high voltage capacitors at 700 (FIG. 5). However, as noted above, this synchronization method may also be employed as the second or subsequent synchronization method.

At 720, in response to completion of charging of the high voltage output capacitors at 700, the synchronization sequence is initiated. The count of the maximum number of synchronization cycles during which the synchronization method will be applied is set to 0 at 722 and the values of the various defined time intervals associated with the synchronization method, including the blanking intervals, X1, X2, X3, X4, X5 and the ventricular escape interval, are set at 724, according to the stored programming within the device. At 726, atrial and ventricular blanking intervals, during which atrial and ventricular events will not be sensed, are initiated, along with timing of intervals X4, X5 and the ventricular escape interval. In the context of a device according to the present invention, the atrial and ventricular blanking intervals may be, for example, set equal to 300 milliseconds, X4 for this first cycle of the synchronization sequence may be set equal to the ventricular escape interval, and the ventricular escape interval may be set to its normal value as employed during VVI pacing. By this expedient, synchronization to a sensed atrial event during the third synchronization interval as discussed above is not possible during the first cycle of the synchronization sequence. At 728 the device checks to see if the escape interval has expired. If so, the device checks at 730 to determine whether the maximum number of synchronization cycles allowed for the synchronization sequence have been reached. If so, a cardioversion or defibrillation shock may optionally be delivered at 732, with the device returning to block 704 (FIG. 5) at 734. Alternatively, the device may simply return to attempt the second or subsequent synchronization method without delivering an atrial cardioversion or defibrillation shock.

Assuming that the maximum of synchronization cycles allowed for the synchronization sequence has not been reached at 730, the device increments the synchronization cycle count at 776, resets the values of the various time intervals employed in conjunction with the synchronization method at 778 and initiates the blanking intervals, time intervals X3, X4, X5 and the escape interval at 780, awaiting the next atrial or ventricular event or expiration of the next escape interval. For the second and subsequent cycles of the synchronization algorithm, X4 may be set to 400–600 milliseconds, X5 may be set to 350–550 milliseconds, and the escape interval may be set at the programmed bradycardia VVI pacing interval. Atrial and ventricular blanking intervals may be set at 100 to 400 milliseconds, depending on upon underlying device programming.

Assuming the escape interval has not expired at 728, the device awaits the occurrence of a sensed atrial event at 736 or a ventricular event at 758. If an atrial event occurs at 736, the timing of a first synchronization interval discussed above is triggered by means of initiation of time intervals X1 and X2 at 738. The device then awaits the occurrence of the expiration of interval X1 or the occurrence of a ventricular event. On expiration of X1 at 740 concurrent with initiation of timing of the first synchronization interval, the device checks to determine whether time interval X4 has previously expired at 742, which allows delivery of a cardioversion or defibrillation shock at 746, synchronized to the time of expiration of X1. Following delivery of such a shock, the device returns to block 704 of FIG. 5 at 748. Because in the first synchronization cycle, X4 is set equal to the ventricular escape interval, X4 will not have expired at X1, during the first synchronization cycle. If X4 has not expired, the device checks at 750 to determine whether time interval X3 has expired at 750. If time interval X3 has expired, then the second synchronization interval available for synchronization to atrial events has expired, and the device awaits the occurrence of a ventricular event at 758, expiration of the escape interval at 728 or sensing of a subsequent atrial event at 736. If X3 has not expired, indicating that X1 expired within the second synchronization interval, the device checks at 752 to determine whether the minimum time interval $X5_p$ initiated following the ventricular event sensed prior to the ventricular event which initiated timing of interval X3 has expired. If so, a shock is delivered at 754, synchronized to the beginning of the first synchronization interval at the expiration of interval X1, and the device returns to block 704 (FIG. 5) at 756. If $X5_p$ has not expired, a shock is not delivered, and the device continues to wait for occurrence of a subsequent ventricular event at 758, expiration of the escape interval at 728 or occurrence of subsequent atrial sensed event at 736. It should be noted in this context that during the first synchronization cycle the time interval $X5_p$ has not previously been initiated and thus does not expire. As such, synchronization to an atrial event occurring prior to expiration of X3 during the first synchronization cycle is not possible.

In response to a ventricular sensed event occurring at 758 the device checks at 764 to determine whether the minimum interval $X5_c$, timed from the immediately preceding ventricular event has expired. If not, no shock is delivered, and the device checks at 760 to determine whether the maximum number "A" of synchronization cycles available for the synchronization sequence has now occurred. If so, the device returns to block 704 of FIG. 5 at 762 to allow for a subsequent synchronization method to be attempted. If not, the next synchronization cycle is initiated by incrementing the synchronization cycle count at 776, setting the values of the time intervals at 778 and initiating the blanking, X3, X4 and escape intervals at 778 and 780 as described above.

If $X5_c$ has expired at 764, the device checks at 768 and 770 to determine whether the first synchronization interval is currently underway. If not, the next synchronization cycle is initiated or the device returns to block 704 of FIG. 5 as described previously. If the ventricular event is sensed during the first synchronization interval after expiration of the minimum time interval $X5_c$, from the preceding ventricular event or charging of the high voltage capacitors, a cardioversion or defibrillation shock is delivered at 772, synchronized to the sensed ventricular event. The device then returns to block 704 (FIG. 5) at 774.

Figure 6C:
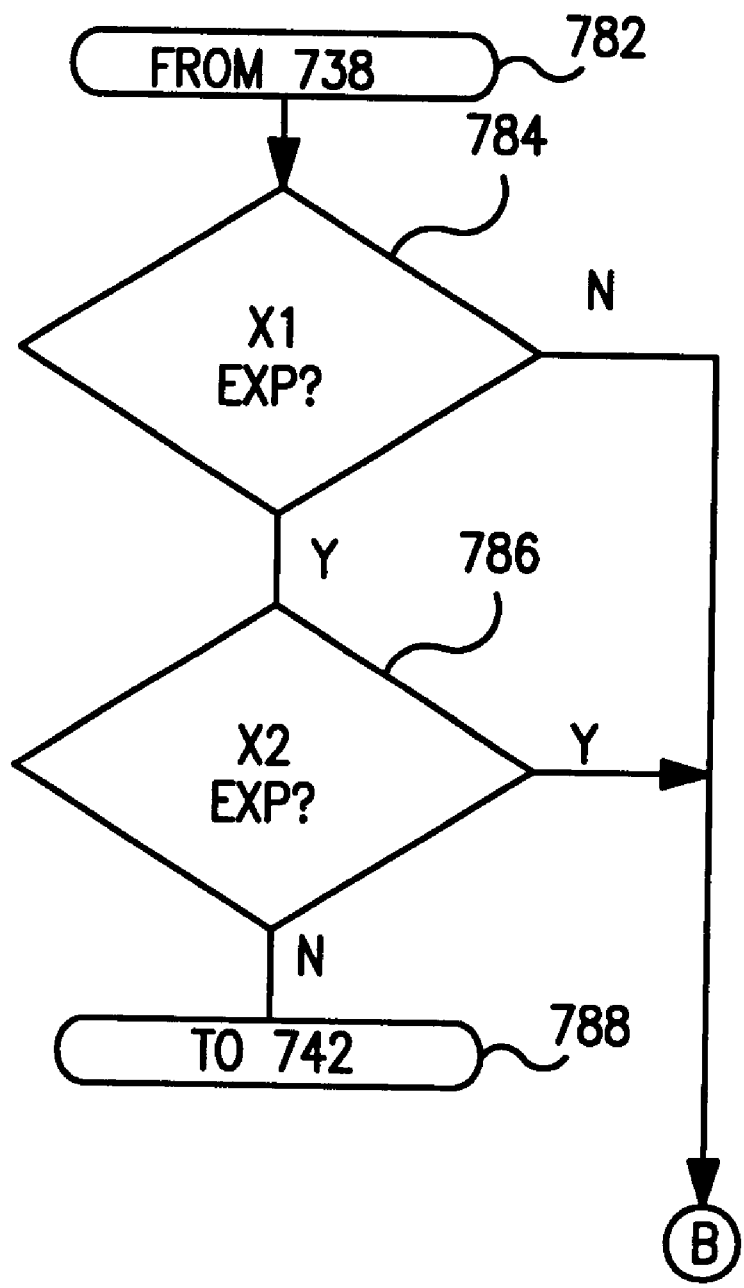

FIG. 6C illustrates an alternative implementation of the synchronization method illustrated in FIGS. 6C–6B. FIG. 6C is a fragmentary functional flow chart which may be substituted for block 740 of FIG. 6A. In this case, rather than attempting to synchronize only to the occurrence of the expiration of interval X1, the device attempts to determine whether the first synchronization interval is underway. If at some time during the first synchronization interval, if either interval X4 has expired or interval X3 has not expired and interval $X5_p$ timed from the second preceding ventricular event has expired, the device will deliver a defibrillation pulse at the earliest time during the first synchronization interval at which these conditions are met. The fragmentary flow chart of FIG. 6C is entered at 782 from block 738 of FIG. 6A at 784 and 786, the device checks to determine whether the first synchronization interval is underway. If so, the device returns to block 742 of flow chart 6A, to determine whether the additional criteria for delivery of a cardioversion or defibrillation shock are met. If the first synchronization interval is not underway, the device awaits sensing of a ventricular event at 758, expiration of the escape interval of 728 or sensing an atrial event at 736. By means of the alternative embodiment illustrated in FIG. 6C, an atrial cardioversion or defibrillation pulse will be delivered at the earliest time that both the first and third synchronization internals are underway or at the earliest time that the first and second synchronization intervals are underway and the minimum time period $X5_p$ has expired.

Figure 7:
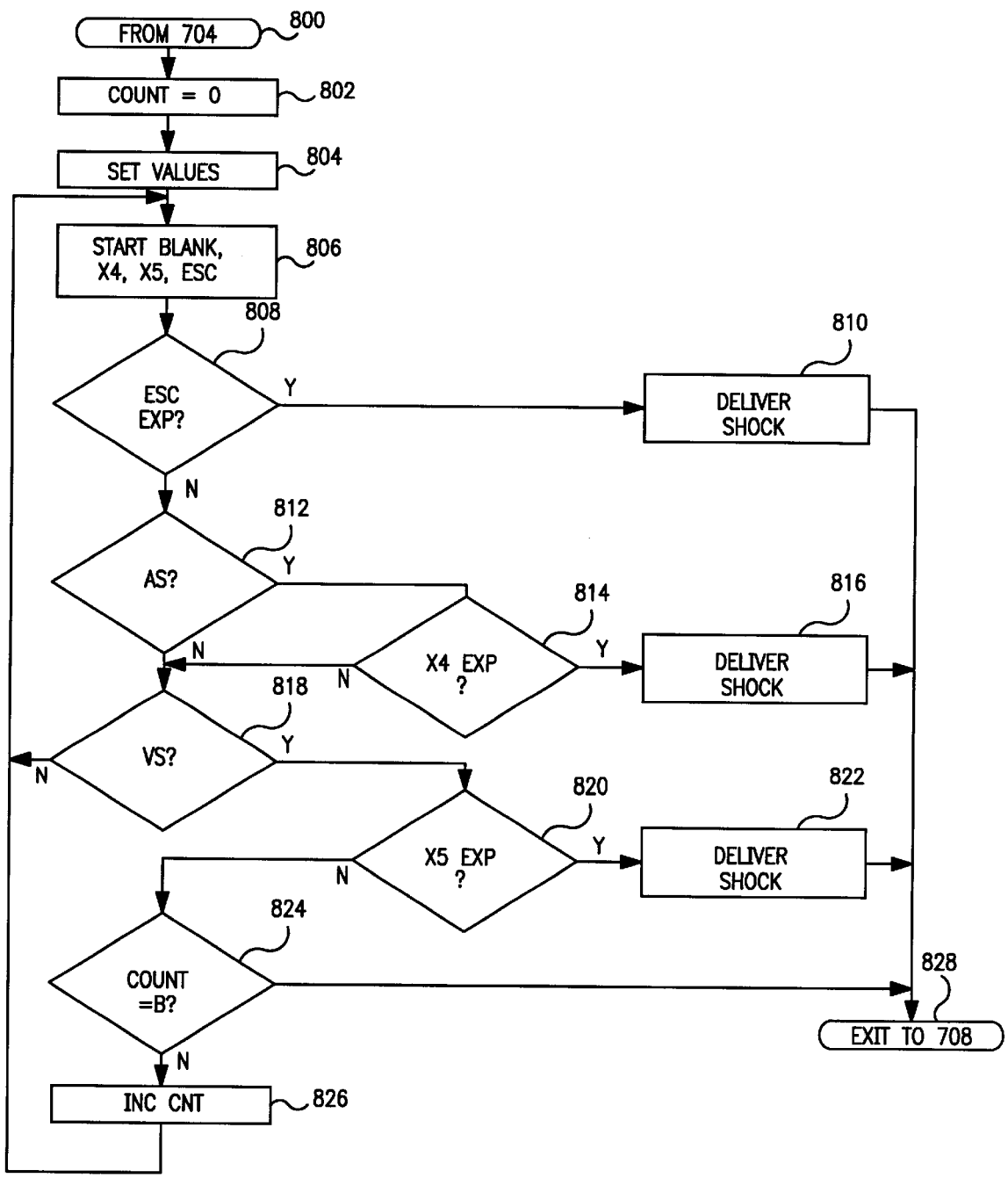
FIG. 7 is a functional flowchart illustrating operation of the additional synchronization method of FIG. 4A.

FIG. 7 is a functional flow chart illustrating the synchronization algorithm illustrated in FIG. 4A. As illustrated, the synchronization sequence is entered at 800, from block 704 (FIG. 5) and corresponds to the second synchronization method 706. The presumption in this case is that the first synchronization method failed to result in delivery of a cardioversion or defibrillation pulse, and this, less restrictive synchronization algorithm will be tried as a second choice.

The first synchronization cycle is initiated at 802 by setting the count of maximum of synchronization cycles allowed for the synchronization sequence to zero, and the values of the various time intervals employed in the synchronization algorithm are set at 804. It should be understood that the event which triggered entry into this second synchronization method was sensing of a ventricular depolarization associated with the end point of the preceding synchronization algorithm, so that the intervals X4, X5, the escape interval and the blanking intervals initiated at 806 are initiated in response to the ventricular event which ended the preceding synchronization sequence. In the context of the present invention, X4 may be 400–600 milliseconds, X5 may be 350–550 milliseconds, the escape interval may be the VVI escape interval as programmed into the device and the blanking intervals may be 100–400 milliseconds in the atrium and the ventricle. At 808 the device checks to determine whether the escape interval has expired. If so, a shock is simply delivered at 810 and the device returns to block 708 of FIG. 5 at 828. In the event that the escape interval has not expired, the device awaits an atrial depolarization or a ventricular depolarization at 812 and 818. In response to sensing of an atrial depolarization, the device checks to determine whether time interval X4 has expired at 814. If so, a shock is delivered at 816, synchronous to the atrial sense event. If the device detects a ventricular depolarization at 818, the device checks to determine whether the time interval X5 timed from the immediately preceding ventricular event has expired at 820. If so, a shock is delivered at 822. If a ventricular event is sensed prior to expiration of minimum interval X5, the device checks at 824 to determine whether the maximum number "B" of synchronization cycles available for this synchronization method has been reached. If so, the device returns to block 708 of FIG. 5 at 828. Otherwise the synchronization cycle count is incremented at 826 and the device awaits expiration of the escape interval at 808, atrial sensing at 812 or ventricular sensing at 818.

Figure 8:
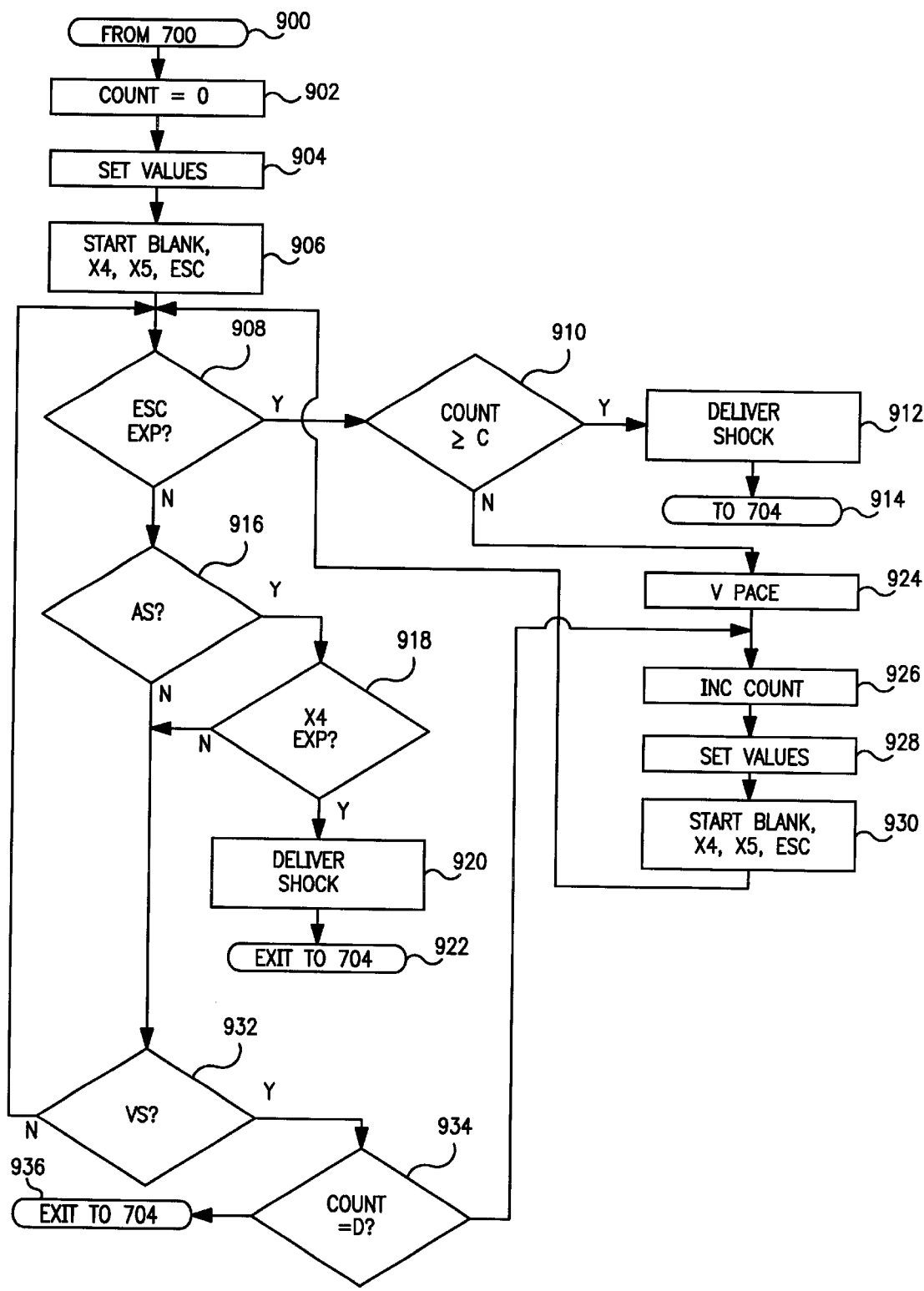
FIG. 8 is a functional flowchart illustrating operation of the additional synchronization method of FIG. 4B.

FIG. 8 is a block functional flow chart of the synchronization algorithm illustrated in FIG. 4B. In this case, it is assumed that this is the initial synchronization algorithm to be employed by the device and that secondary synchronization methods corresponding to those illustrated in FIG. 4a and FIGS. 3A–3B may be employed if synchronization is not possible using the method illustrated in FIG. 8. The synchronization sequence is initiated at 900 after charging of the output capacitors at 700 (FIG. 5). The count of synchronization cycles allowed during the synchronization sequence is set to 0 at 902. The values of the various time intervals employed by the synchronization sequence are set at 904, and blanking, X4, X5 and escape intervals are initiated at 906. For purposes of this synchronization algorithm, X4 may be set equal to the escape interval for the first synchronization cycle, X5 may be 350–550 milliseconds, the escape interval may be the programmed VVI pacing escape interval, and the blanking intervals may be, for example, 100–400 milliseconds.

The device checks at 908 to determine whether the escape interval has expired, if so, the device checks at 910 to determine whether a defined number "C" of R-R intervals has been reached or exceeded at 910. If so, a shock is delivered at 912 synchronized to the expiration of the escape interval and the device returns to block 704 (FIG. 5) at 914. If less than "C" R-R intervals have occurred, the device delivers a pacing pulse at 924 on expiration of the escape interval, the count of R-R intervals is incremented at 926, the values of the time periods are reset at 928 and the blanking, X4, X5 and escape intervals are reset at 930. For purposes of the present invention the blanking intervals may be 100–400 milliseconds, X4 may be 400–600 milliseconds, X5 may be 350–550 milliseconds, and the escape interval may be the underlying VVI pacing rate. The device then awaits the expiration of the next escape interval at 908, atrial sensing at 916 or ventricular sensing at 932.

If an atrial event is sensed at 916, the device checks to determine whether time interval X4 has expired at 918. If so, a shock is delivered at 920, synchronized to the sensed atrial event and the device returns to block 704 (FIG. 5) at 922. If X4 has not expired, the device awaits a ventricular sense at 932, expiration of the escape interval at 908 or a subsequent atrial sense at 916.

If the device senses a ventricular event at 932, the device checks to determine whether the synchronization cycle count is indicative of the maximum number "D" of synchronization cycles allowed for the synchronization sequence. "D" preferably is 2–10 synchronization cycles greater than "C", to allow for multiple attempts at cardioversion on expiration of the escape interval. If "D" synchronization cycles have occurred the device exits to block 704 (FIG. 5) at 936 in order to begin the next synchronization sequence. If not, the count is incremented at 926, the values of the intervals employed in the synchronization sequence are employed at 928 and the blanking, X4, X5 and escape intervals are initiated at 930. This process continues until either a shock is delivered or the maximum number "D" of cycles allowed for the synchronization sequence has been reached.

The above disclosure sets forth a device in which sensed events in the atrium and ventricle are used to control delivery of electrical therapy to treat tachyarrhythmias. Although it seems likely that commercial embodiments of such a device will require the use of a microprocessor in order to perform the numerous calculations and analysis steps required, it is within the realm of possibility that some or all of the detection criteria provided by the microprocessor in the above disclosure might instead be provided by means of a fill custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties. Thus, the above description should be considered exemplary, rather than limiting, with regard to the interpretation of the following claims.

In conjunction with the above disclosure, we claim:

1. A method of atrial defibrillation, comprising:

sensing atrial events;

sensing ventricular events;

sensing atrial tachyarrhythmia;

defining a first synchronization interval initiated following a sensed atrial event;

defining a second synchronization interval initiated responsive to a sensed ventricular event; and delivering an atrial defibrillation pulse responsive to the first and second synchronization intervals simultaneously being concurrently underway.

2. A method according to claim 1 wherein delivering an atrial defibrillation pulse comprises delivering an atrial defibrillation pulse responsive to initiation of the first synchronization interval during the second synchronization interval.

3. A method according to claim 1 or claim 2, further comprising:

defining minimum time intervals following ventricular events; and delivering an atrial defibrillation pulse responsive to expiration of the minimum time interval following a ventricular event preceding the sensed ventricular event which initiated the second synchronization interval currently underway.

4. A method according to claim 1 or claim 2, further comprising defining a first time interval initiated responsive to a sensed atrial event and wherein defining the first synchronization interval comprises the first synchronization interval to initiate on expiration of the first time interval.

5. A method according to claim 4 wherein delivering delivering an atrial defibrillation pulse comprises delivering an atrial defibrillation pulse responsive to initiation of the second synchronization interval during the first synchronization interval.

6. A method according to claim 1 wherein:

defining the first synchronization interval comprises initiating the first synchronization interval on expiration of a first time interval following a sensed atrial event;

defining the second synchronization interval comprises initiating the second synchronization interval on expiration of a second time interval following a sensed ventricular event; and delivering an atrial defibrillation pulse comprises delivering an atrial defibrillation pulse responsive to the first and second synchronization intervals being concurrently underway.

7. A method according to claim 6 wherein delivering an atrial defibrillation pulse comprises delivering an atrial defibrillation pulse responsive to initiation of the first synchronization interval during the second synchronization interval.

8. A method of atrial cardioversion, comprising:

sensing atrial events;

sensing ventricular events;

sensing atrial tachyarrhythmia;

defining a first synchronization interval initiated following a sensed atrial event;

defining a second synchronization interval initiated responsive to a sensed ventricular event; and delivering an atrial cardioversion pulse responsive to the first and second synchronization intervals simultaneously being concurrently underway.

9. A method according to claim 8 wherein delivering an atrial cardioversion pulse comprises delivering an atrial cardioversion pulse responsive to initiation of the first synchronization interval during the second synchronization interval.

10. A method according to claim 8 or claim 9, further comprising:

defining minimum time intervals following ventricular events; and delivering an atrial cardioversion pulse responsive to expiration of the minimum time interval following a ventricular event preceding the sensed ventricular event which initiated the second synchronization interval currently underway.

11. A method according to claim 8 or claim 9, further comprising defining a first time interval initiated responsive to a sensed atrial event and wherein defining the first synchronization interval comprises the first synchronization interval to initiate on expiration of the first time interval.

12. A method according to claim 11 wherein delivering an atrial cardioversion pulse comprises delivering an atrial cardioversion pulse responsive to initiation of the second synchronization interval during the first synchronization interval.

13. A method according to claim 8 wherein:

defining the first synchronization interval comprises initiating the first synchronization interval on expiration of a first time interval following a sensed atrial event;

defining the second synchronization interval comprises initiating the second synchronization interval on expiration of a second time interval following a sensed ventricular event; and delivering an atrial cardioversion pulse comprises delivering an atrial cardioversion pulse responsive to the first and second synchronization intervals simultaneously being concurrently underway.

14. A method according to claim 13 wherein delivering an atrial cardioversion pulse comprises delivering an atrial cardioversion pulse responsive to initiation of the first synchronization interval during the second synchronization interval.

* * * * *